US011834396B2

(12) United States Patent
Erdelmeier et al.

(10) Patent No.: US 11,834,396 B2
(45) Date of Patent: Dec. 5, 2023

(54) METHOD FOR SYNTHESIZING 3,5-DIIODO-4-HYDROXY BENZYL ALCOHOL

(71) Applicant: INNOVERDA, Villejuif (FR)

(72) Inventors: Irène Erdelmeier, Paris (FR); Sylvain Daunay, Le Perreux sur (FR)

(73) Assignee: INNOVERDA, Villejuif (FR)

( * ) Notice: Subject to any disclaimer, the term of this patent is extended or adjusted under 35 U.S.C. 154(b) by 0 days.

(21) Appl. No.: 18/021,143

(22) PCT Filed: Sep. 6, 2021

(86) PCT No.: PCT/EP2021/074440
§ 371 (c)(1),
(2) Date: Feb. 13, 2023

(87) PCT Pub. No.: WO2022/053418
PCT Pub. Date: Mar. 17, 2022

(65) Prior Publication Data
US 2023/0286890 A1      Sep. 14, 2023

(30) Foreign Application Priority Data
Sep. 8, 2020 (FR) .................................. 2009106

(51) Int. Cl.
*C07C 39/27* (2006.01)
*C07C 37/62* (2006.01)

(52) U.S. Cl.
CPC .................................. *C07C 37/62* (2013.01)

(58) Field of Classification Search
CPC .................................................... C07C 37/62
See application file for complete search history.

(56) References Cited

U.S. PATENT DOCUMENTS

| | | | |
|---|---|---|---|
| 8,766,003 B2 | 7/2014 | Citterio et al. | |
| 2022/0119336 A1 | 4/2022 | Omatsu et al. | |

FOREIGN PATENT DOCUMENTS

| | | | | |
|---|---|---|---|---|
| WO | 9522992 A2 | 8/1995 | | |
| WO | 2013010102 A2 | 1/2013 | | |
| WO | 2020137935 A1 | 7/2020 | | |
| WO | WO-2021157551 A1 * | 8/2021 | ............. | C07C 39/15 |

OTHER PUBLICATIONS

WO2021157551A1, machine translation, Aug. 2021, pp. 1-49 (Year: 2021).*
WO2020137935A1, machine translation, Jul. 2020, pp. 1-48 (Year: 2020).*
Gregorz M. Salamonczyk et al., "A concise synthesis of thyroxine (T4) and 3,5,3'-Triiodo-I-thyronine (T3)," Tetrahedron Letters, Oct. 6, 1997, pp. 6965-6968, vol. 38, No. 40, Elsevier.
Teruo Matsuura et al., "Model Reactions for the Biosynthesis of Thyroxine. I. Structural Influence of the Side Chain in Analogs of Diiodotyrosine on their Conversion to Analogs of Thyroxine," J. Am. Chem. Soc., Mar. 1, 1959, pp. 871-878, vol. 81, issue 4, JACS.
Etienne Andre et al., "A new, Simple and Versatile Strategy for the Synthesis of Short Segments of Zigzag-Type Carbon Nanotubes," Chem. Eur. J., Jan. 2016, pp. 3105-3114, vol. 22, Wiley.
Michael F. McLaughlin et al., "Phenolic Oxidation Using H2O2 via in Situ Generated para-Quinone Methides for the Preparation of para-Spiroepoxydienones," Org. Lett., Aug. 16, 2019, pp. 6504-6507, vol. 21. No. 16, American Chemical Society.
P. Claus et al., "Darstellung und Oxydation von Hydroxybenzylakoholen," Monatsh. Chem., 1972, pp. 1178-1193, vol. 103.
T. A. Henry et al., "CXXVIII.—Mercury compounds of hydroxybenzaldehydes," J. Chem. Soc., Trans., 1922, pp. 1055-1060, vol. 121.
Rafael D.C. Gallo et al., "Efficient and Selective Iodination of Phenols Promoted by Iodine and Hydrogen Peroxide in Water," J. Braz. Chem. Soc., 2010, pp. 770-774, vol. 21, No. 4. http://dx.doi.org/10.1590/S0103-50532010000400026.
C. Paal, "Zur Kenntniss des p-Oxybenzaldehyds," Chem. Ber., 1895, pp. 2407-2414, vol. 28.

* cited by examiner

*Primary Examiner* — Medhanit W Bahta
(74) *Attorney, Agent, or Firm* — H&I PARTNERS; C. Andrew Im; Jean-Christophe Hamann

(57) ABSTRACT

A method for synthesizing 4-hydroxy-3,5-diiodobenzyl alcohol. The synthesis method includes, in just one step, the synthesis of 4-hydroxy-3,5-diiodobenzyl alcohol from 4-hydroxybenzylalcohol, in an aqueous medium at an initial pH of at least 7, containing at least 2 equivalents of diiodide. The method is simple and makes it possible to achieve very good yields at a lower cost.

15 Claims, No Drawings

METHOD FOR SYNTHESIZING 3,5-DIIODO-4-HYDROXY BENZYL ALCOHOL

RELATED APPLICATIONS

This application is a § 371 application of PCT/EP2021/074440 filed Sep. 6, 2021, which claims priority from French Patent Application No. 2009106 filed Sep. 8, 2020, each of which is incorporated herein by reference in its entirety.

FIELD OF THE INVENTION

The invention relates to a new method for synthesizing 4-hydroxy-3,5-diiodobenzyl alcohol or 4-hydroxy-3,5-diiodo-benzenemethanol, CAS No. 37987-26-1, of Formula 1,

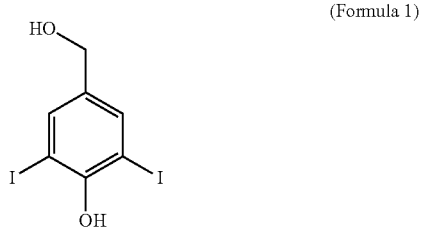 [SMILES: OCc1cc(I)c(O)c(I)c1]

(Formula 1)

which is a compound of importance for the study of the metabolism of the hormone L-thyroxine, as well as a possible synthesis intermediate, in particular of Levothyrox.

BACKGROUND OF THE INVENTION

The synthesis described in the literature takes place in two steps, proceeding from 4-hydroxybenzylaldehyde:
1. Iodination with ICl:

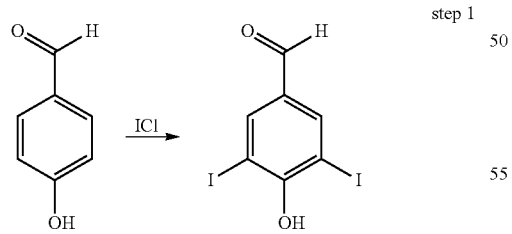

Described in WO9522992A2 (page 28), WO2013010102A2 (page 98, 85%), Tetrahedr. Lett. 1997, 38 (40), 6965 and JACS 1959, 81, 871 (without yield), and also J. Chem. Soc. 1922, 121, 1055 (via the preparation of a mercury derivative then reaction with KI/I2), and with I2/HIO3 in Chem. Ber. 1895, 2407.

2. Reduction in alcohol:

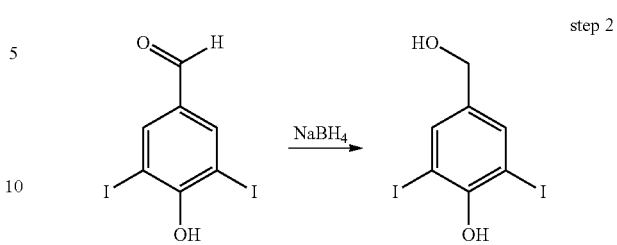

Described in WO9522992A2 (page 30, with BH3), WO2013010102A2 (page 99), Tetrahedr. Lett. 1997, 38 (40), 6965, and Chem. Eur. J. 2016, 22, 3105 (in the Supporting Information page 115, 99%), and Org. Lett. 2019, 21, 6504 and Monatsh. Chem. (1972), 103(4), 1178-93.

OBJECT AND SUMMARY OF THE INVENTION

The main aim of the invention is that of solving the technical problem of providing a new method of synthesizing, in just one step, the compound of formula 1 above.

Another main aim of the invention is that of solving the technical problem of providing a new method for synthesizing, in just one step, the compound of formula 1 above, with excellent yields.

Another main aim of the invention is that of solving the technical problem of providing a new method for synthesizing, in just one step, the compound of formula 1 above, at ambient temperature, with excellent yields, and according to a simple and low-cost solution, which can be used on an industrial scale.

DETAILED DESCRIPTION OF THE INVENTION

The invention solves, for the first time, all the technical problems set out above, in a simple, low-cost manner, which can be used on an industrial scale.

Thus, according to a first aspect, the present invention provides a method for synthesizing 4-hydroxy-3,5-diiodo-benzyl alcohol, characterized in that it comprises the synthesis, in just one step, of 4-hydroxy-3,5-diiodo-benzyl alcohol of Formula 1

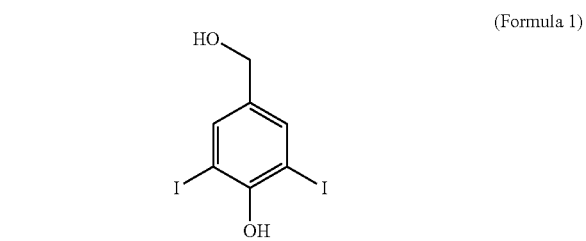 [SMILES: OCc1cc(I)c(O)c(I)c1]

(Formula 1)

from 4-hydroxybenzylalcohol, in aqueous solution at an initial pH of at least 7, containing at least 2 equivalents of iodizing agent, in particular iodine or diiodide.

The direct iodination and the direct diiodination of other molecules of the phenol type are known, but, in a general manner, oxidizing reaction conditions are required, such as the presence of HIO3, H2O2, etc., see in particular references 9 and 10.

The invention implements, in a manner entirely surprising to a person skilled in the art, direct diiodination of 4-hydroxybenzylalcohol.

The use of 4-hydroxybenzylalchohol is not obvious to a person skilled in the art, since the prior art teaches iodination in the presence of an oxidizing agent, and a person skilled in the art would have to expect that the benzyl alcohol function would be oxidized in these conditions. Furthermore, a person skilled in the art would also have to expect that it would be difficult to stop at the di-iodized derivative, on account of the fact that this is a phenolic derivative rich in electrons, and thus very reactive with respect to an electrophilic substitution, which is less the case for the aldehyde derivative recommended by persons skilled in the art since 1895, see reference 11, and also from 1959, see reference 4, i.e. for more than 120 years.

There has therefore been a real bias, in the art, towards performing direct diiodination of 4-hydroxybenzylalcohol.

Furthermore, within the scope of the invention said deiodination is achieved in just one step, at excellent yields, i.e. at least 75%, which has never been achieved previously, and simply using an iodizing agent, in particular iodine, without adding an oxidant.

According to a variant of the method according to the invention, the reaction takes place at ambient temperature. It is also surprising according to the invention, as shown by the following examples, that even at ambient temperature the reaction duration is short, in the region of 2 hours, resulting in a method that is excellent for low-cost industrial production.

According to a particular embodiment, the method is characterized in that the initial pH is set to at least 7, by adding a weak base, in particular selected from disodium hydrogen phosphate (Na2HPO4), KHCO3, or K2HPO4.

According to another particular embodiment, the method is characterized in that the initial pH of the aqueous solution is between 7 and 11.

According to yet another particular embodiment, the method is characterized in that the initial pH of the aqueous solution is between 7 and 9.

According to another particular embodiment, the method is characterized in that at least 2 equivalents of a weak base are used, said base in particular being selected from disodium hydrogen phosphate (Na2HPO4), KHCO3, or K2HPO4.

According to another particular embodiment, the method is characterized in that the aqueous solution comprises at least one water soluble alcohol.

According to yet another particular embodiment, the method is characterized in that the proportion by weight of water soluble alcohol in the aqueous solution is between greater than zero and approximately 25%.

According to a particular variant, the proportion by weight of water soluble alcohol in the aqueous solution is between 5 and 20%.

According to another particular variant, the proportion by weight of water soluble alcohol in the aqueous solution is between 5 and 15%.

According to another particular variant, the proportion by weight of water soluble alcohol in the aqueous solution is approximately 10%.

According to another particular variant, the method is characterized in that the water soluble alcohol is an alcohol low in C1-C6, in particular selected from methanol, ethanol, propanol, isopropanol, butanol, pentanol.

According to a particular embodiment, the method is characterized in that the aqueous solution comprises a mixture selected from water/ethanol 9/1, water/methanol 9/1, water/propanol or isopropanol 9/1.

According to another particular embodiment, the method is characterized in that the reaction takes place in the absence of oxidizing agent(s).

According to yet another particular embodiment, the method is characterized in that the aqueous solution is single-phase.

According to yet another particular embodiment, the method is characterized in that the following chemical reaction is carried out:

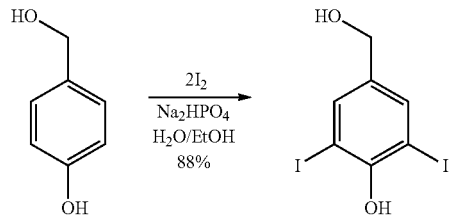 [SMILES: OCc1ccc(O)cc1 ; OCc1cc(I)c(O)c(I)c1]

Other aims, features and advantages of the invention will become clear to a person skilled in the art in light of the embodiments of the invention given below, by way of illustration, and which are in no way intended to limit the scope of the invention defined by the claims. In the description, including the examples and the claims, the pressure is atmospheric pressure, the temperature is given in degrees Celsius, the percentages are given in weight, unless otherwise indicated. The ambient temperature is normal room temperature, including an air-conditioned room; it is understood by a person skilled in the art as being generally between 18° C. and 25° C.

EXPERIMENTAL PART

I. Examples According to the Invention

Example 1 According to the Invention: Optimal Protocol 12.41 g (100 mmol) 4-hydroxybenzyl alcohol, 39.95 g (220 mmol) of disodium hydrogen phosphate, and 56.4 g (220 mmol) iodine are dissolved in 100 ml absolute ethanol and 900 ml demineralized water. The initial pH of the solution is 8. Stirring strongly, the solution is stirred at ambient temperature for at least 2 hours. 8.8 ml (100 mmol) concentrated hydrochloric acid is added to the reaction medium in order to obtain a pH of 3. The suspension obtained is filtered, and the solid obtained is washed using 50 ml of a 5% thiosulfate solution, and 3 times using 50 ml water. 32.8 g (88%) 4-hydroxy-3,5-diiodobenzyl alcohol in the form of a powder is obtained after drying. The 1H-NMR spectrum is consistent with the structure and the literature [ref. 5].

1H-NMR (400 MHz, DMSO-d6) δ9.40 (s, 1H), 7.67 (s, 2H), 5.20 (t, J=5.5 Hz, 1H), 4.35 (d, J=5.5 Hz, 2H).

Example 2 According to the Invention: Change of the Base Added: KHCO3

1.24 g (10 mmol) 4-hydroxybenzyl alcohol, 2.22 g (22 mmol) potassium hydrogen carbonate, and 5.64 g (22 mmol) iodine are dissolved in 10 ml absolute ethanol and 90 ml demineralized water. The initial pH of the solution is 8.7. Stirring strongly, the solution is stirred at ambient temperature for at least 2 hours. Following dilution by addition of 100 ml water, the suspension obtained is filtered, and the solid obtained is washed using 20 ml of a 5% thiosulfate solution, and 3 times using 20 ml water. 3.20 g (85%) 4-hydroxy-3,5-diiodobenzyl alcohol in the form of a powder is obtained after drying.

Example 3 According to the Invention: Change of the Base Added: K2HPO4

1.24 g (10 mmol) 4-hydroxybenzyl alcohol, 3.83 g (22 mmol) dipotassium hydrogen phosphate, and 5.64 g (22 mmol) iodine are dissolved in 10 ml absolute ethanol and 90 ml demineralized water. The initial pH of the solution is 7.5. Stirring strongly, the solution is stirred at ambient temperature for at least 2 hours. Following dilution by addition of 100 ml water, the suspension obtained is filtered, and the solid obtained is washed using 20 ml of a 5% thiosulfate solution, and 3 times using 20 ml water. 3.12 g (83%) 4-hydroxy-3,5-diiodobenzyl alcohol in the form of a powder is obtained after drying.

Example 4 According to the Invention: Change of the Water Soluble Alcohol: Methanol in Place of Ethanol Proceeding as described in example 1, using an aqueous solution of methanol and water in a ratio of 10/90, 4-hydroxy-3,5-diiodobenzyl alcohol is obtained in the form of a powder, following drying, at a yield of 85%.

Example 5 According to the Invention: Change of the Water Soluble Alcohol: Isopropanol in Place of Ethanol Proceeding as described in example 1, using an aqueous solution of isopropanol and water in a ratio of 10/90, 4-hydroxy-3,5-diiodobenzyl alcohol is obtained in the form of a powder, following drying, at a yield of 87%.

Example 6 According to the Invention: Change of the Medium, Using an Aqueous Solution without Water Soluble Alcohol Proceeding as described in example 1, using an aqueous solution of without alcohol, 4-hydroxy-3,5-diiodobenzyl alcohol is obtained in the form of a powder, following drying, at a yield of 88%, containing approximately 5% monoiodized by-product.

Example 7 According to the Invention: Change of the Water/Alcohol Ratio to 95/5 in Place of 90/10

Proceeding as described in example 1, using an aqueous solution of ethanol and water in a ratio of 5:95, 4-hydroxy-3,5-diiodobenzyl alcohol is obtained in the form of a powder, following drying, at a yield of 82%.

Example 8 According to the Invention: Change of the Water/Alcohol Ratio to 80/20 in Place of 90/10

Proceeding as described in example 1, using an aqueous solution of ethanol and water in a ratio of 20:80, 4-hydroxy-3,5-diiodobenzyl alcohol is obtained in the form of a powder, following drying, at a yield of 78%.

II. Comparative Examples

Example 9 COMPARATIVE EXAMPLE 1: Change of the Base Added: Sodium Acetate 1.24 g (10 mmol) 4-hydroxybenzyl alcohol, 1.82 g (22 mmol) of sodium acetate, and 5.13 g (20 mmol) diiodine are dissolved in 10 ml absolute ethanol and 90 ml demineralized water. The initial pH of the solution is 6. Stirring strongly, the solution is stirred at ambient temperature for at least 2 hours. The suspension obtained is filtered, and the solid obtained is washed using 20 ml of a 5% thiosulfate solution, and 3 times using 20 ml water. 2.03 g (53%) 4-hydroxy-3,5-diiodobenzyl alcohol in the form of a powder is obtained after drying.

Example 10 COMPARATIVE EXAMPLE 2: Change of the Base Added: Sodium dihydrogen phosphate Proceeding as described in example 1, but using 2.2 equiv. NaH2PO4 in place of 2.2 equiv. Na2HPO4, the initial pH of the solution is 4.5. The desired product is formed, but in a small amount (<30%), and cannot be isolated by precipitation.

Example 11 COMPARATIVE EXAMPLE 3: Change of the Base Added: Potassium dihydrogen phosphate Proceeding as described in example 1, but using 2.2 equiv. KH2PO4 in place of 2.2 equiv. Na2HPO4, the initial pH of the solution is 4. The desired product is formed in a trace amount (<15%), and cannot be isolated by precipitation.

Example 12 COMPARATIVE EXAMPLE 4: Change of Equivalent of 12

1.24 g (10 mmol) 4-hydroxybenzyl alcohol, 3.83 g (22 mmol) of disodium hydrogen phosphate, and 3.58 g (14 mmol) diiodine are dissolved in 10 ml absolute ethanol and 90 ml demineralized water. The initial pH of the solution is 8.5. Stirring strongly, the solution is stirred at ambient temperature for 20 hours. 100 ml water is added to the reaction medium, and then the suspension obtained is recovered by filtration and washed using 20 ml of a 5% thiosulfate solution, and 3 times using 20 ml water. 2.06 g (55%) 4-hydroxy-3,5-diiodobenzyl alcohol in the form of a powder is obtained after drying.

It is observed that the reaction time of 20 hours required in comparison with 2 hours within the scope of the invention is incompatible with low-cost industrial production.

Example 13 COMPARATIVE EXAMPLE 5: Change of the Reaction Temperature: 60° C. in Place of Ambient temperature Proceeding as described in example 1, but heating the medium to 60° C. for one hour, 4-hydroxy-3,5-diiodobenzyl alcohol is formed (approximately 50%), with degradation products.

Example 14 COMPARATIVE EXAMPLE 6: Change of the Water/Ethanol Ratio to 70/30 in Place of 90/10

1.24 g (10 mmol) 4-hydroxybenzyl alcohol, 3.83 g (22 mmol) disodium hydrogen phosphate, and 5.12 g (20 mmol)

diiodine are dissolved in 30 ml absolute ethanol and 70 ml demineralized water. The initial pH of the solution is 8.5. Stirring strongly, the solution is stirred at ambient temperature for 20 hours. 100 ml water is added to the reaction medium, and then the suspension obtained is filtered, and the solid obtained is washed using 20 ml of a 5% thiosulfate solution, and 3 times using 20 ml water. 2.13 g (57%) 4-hydroxy-3,5-diiodobenzyl alcohol in the form of a powder is obtained after drying.

Example 15 COMPARATIVE EXAMPLE 7: Change of the Water/Ethanol Ratio to 50/50 in Place of 90/10

Proceeding as described in example 1, using an aqueous solution of ethanol and water in a ratio of 50/50, 4-hydroxy-3,5-diiodobenzyl alcohol is present at a low yield (<20%). Mainly degradation products are detected.

Example 16 COMPARATIVE EXAMPLE 8: Reaction in a Non-Aqueous Ethanolic Solution 1.24 g (10 mmol) 4-hydroxybenzyl alcohol, 2.27 g (22 mmol) triethylamine, and 5.64 g (22 mmol) diiodine are dissolved in 100 ml absolute ethanol. The initial pH is 8.5. Stirring strongly, the solution is stirred at ambient temperature for 2 hours. The 4-hydroxy-3,5-diiodobenzyl alcohol is present at low yield (<25%). Mainly degradation products are detected.

REFERENCES

1. Blaney, Jeffrey M.; Cohen, Fred; PCT Int. Appl. (1995), WO 9522992 A2.
2. Latham, Keith R; PCT Int. Appl. (2013), WO 2013010102 A2.
3. Salamonczyk, Grzegorz M.; Oza, Vibha B.; Sih, Charles J.; Tetrahedr. Lett. 1997, 38 (40), 6965.
4. Teruo Matsuura and H. J. Cahnmann; JACS 1959, 81, 871.
5. Etienne André, Baptiste Boutonnet, Pauline Charles, Cyril Martini, JuanManuel Aguiar-Hualde, Sylvain Latil, Vincent Gurineau, Karim Hammad, Priyanka Ray, Régis Guillot and Vincent Huc; Chem. Eur. J. 2016, 22, 3105.
6. Michael F. McLaughlin, Elisabetta Massolo, Thomas A. Cope, and Jeffrey S. Johnson; Org. Lett. 2019, 21, 6504.
7. P. Claus, P. Schilling, J. S. Gratzl, K. Kratzl; Monatsh. Chem. (1972), 103(4), 1178.
8. T. A. Henry, T. M. Sharp; J. Chem. Soc., Trans. 1922, 121, 1055.
9. Citterio, A.; Battistini, E.; Belnome, D.; Buonsanti, F.; Lattuada, L.; Leonardi, G.; Uggeri, F.; Vignale, E.; Visigalli, M. Process for the iodination of phenolic derivatives; U.S. Pat. No. 8,766,003, Jul. 1, 2014.
10. Gallo, R. D. C.; Gebara, K. S.; Muzzi, R. M.; Raminelli, C. Efficient and Selective Iodination of Phenols Promoted by Iodine and Hydrogen Peroxide in Water. Journal of the Brazilian Chemical Society 2010, 21 (4), 770-774. http://dx.doi.org/10.1590/S0103-50532010000400026
11. C. Paal, Chem. Ber. 1895, 28, 2407-2414.

The invention claimed is:

1. A method for synthesizing 4-hydroxy-3,5-diiodobenzyl alcohol, comprising the synthesis, in just one step, of 4-hydroxy-3,5-diiodo-benzyl alcohol of formula 1

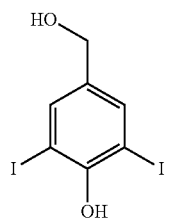 [SMILES: OCc1cc(I)c(O)c(I)c1]

from 4-hydroxybenzylalcohol, in an aqueous solution having an initial pH of at least 7, containing at least 2 equivalents of iodizing agent.

2. The method of claim 1, wherein the iodizing agent is an iodine or a diiodide.

3. The method of claim 1, wherein the initial pH is set by addition of a weak base.

4. The method of claim 3, wherein the weak base is selected from disodium hydrogen phosphate (Na2HPO4), KHCO3, or K2HPO4.

5. The method of claim 1, wherein the initial pH of the aqueous solution is between 7 and 11.

6. The method of claim 1, wherein the initial pH of the aqueous solution is between 7 and 9.

7. The method of claim 1, wherein said at least 2 equivalents of weak base are used, the weak base being selected from disodium hydrogen phosphate (Na2HPO4), KHCO3, or K2HPO4.

8. The method of claim 1, wherein the aqueous solution comprises at least one water soluble alcohol at a proportion by weight of between more than zero and 25%.

9. The method of claim 1, wherein the aqueous solution comprises at least one water soluble alcohol, at a proportion by weight of between 5 and 20%.

10. The method of claim 1, wherein the aqueous solution comprises at least one water soluble alcohol, at a proportion by weight of between 5 and 15%.

11. The method of claim 8, wherein the water soluble alcohol is an alcohol low in C1-C6, selected from methanol, ethanol, propanol, isopropanol, butanol or pentanol.

12. The method of claim 1, wherein the aqueous solution comprises a mixture selected, in volume, from water/ethanol 9/1, water/methanol 9/1, water/propanol or isopropanol 9/1.

13. The method of claim 1, wherein a reaction of the synthesis takes place in the absence of an oxidizing agent.

14. The method of claim 1, wherein a reaction of the synthesis takes place at an ambient temperature.

15. The method of claim 1, wherein the following chemical reaction is carried out:

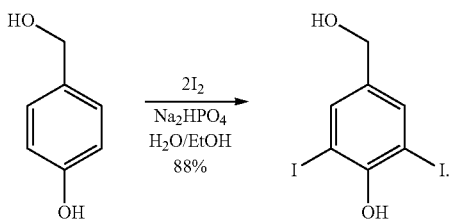 [SMILES: OCc1ccc(O)cc1 ; OCc1cc(I)c(O)c(I)c1]

* * * * *